US009528943B2

(12) United States Patent
Medico

(10) Patent No.: US 9,528,943 B2
(45) Date of Patent: Dec. 27, 2016

(54) DEVICE AND METHOD FOR DETECTING AND/OR DETERMINING THE POSITION OF A BARRIER LAYER CONTAINED IN THE WALL OF A TUBULAR PACKAGING MATERIAL

(75) Inventor: Leonard Medico, Vionnaz (CH)

(73) Assignee: AISAPACK HOLDING S.A., Vouvry (CH)

( * ) Notice: Subject to any disclaimer, the term of this patent is extended or adjusted under 35 U.S.C. 154(b) by 0 days.

(21) Appl. No.: 14/111,423

(22) PCT Filed: Apr. 4, 2012

(86) PCT No.: PCT/IB2012/051650
§ 371 (c)(1),
(2), (4) Date: Dec. 9, 2013

(87) PCT Pub. No.: WO2012/140546
PCT Pub. Date: Oct. 8, 2012

(65) Prior Publication Data
US 2014/0309094 A1      Oct. 16, 2014

(30) Foreign Application Priority Data

Apr. 15, 2011  (EP) .................................... 11162538

(51) Int. Cl.
*G01N 21/90*   (2006.01)
*G01N 21/84*   (2006.01)
*B65B 57/00*   (2006.01)

(52) U.S. Cl.
CPC ............... *G01N 21/90* (2013.01); *B65B 57/00* (2013.01); *G01N 21/8422* (2013.01); *G01N 21/9072* (2013.01); *G01N 21/9081* (2013.01)

(58) Field of Classification Search
CPC .. G01B 11/0625; G01N 21/90; G01N 21/9081
USPC ............... 356/3.01–3.15, 4.01–4.1, 5.01–5.15,356/6–22, 28, 28.5
See application file for complete search history.

(56) References Cited

U.S. PATENT DOCUMENTS 4,304,995 A     12/1981  Huttunen et al.
5,259,716 A *   11/1993  Hoshino ................. B29C 49/78
                                                   198/394
6,967,716 B1 *  11/2005  Cochran ................. G01N 21/31
                                                   250/223 B
2006/0208172 A1* 9/2006  Akkerman et al. ....... 250/223 B
2009/0010385 A1* 1/2009  Ott ..................... G01B 11/0625
                                                   378/54

FOREIGN PATENT DOCUMENTS

| FR | 2 435 696 | 4/1980 |
|---|---|---|
| JP | 55-43492 A | 3/1980 |
| JP | 2001-48145 A | 2/2001 |
| JP | 2002-543379 A | 12/2002 |
| JP | 2005-49258 A | 2/2005 |
| JP | 2009-156822 | 7/2009 |
| JP | 2010-32374 A | 2/2010 |
| WO | 00/65327 A1 | 11/2000 |
| WO | WO 00/65327 | 11/2000 |

OTHER PUBLICATIONS

P. Mercer "Measurement and Control of Barrier Layers", Tappi Journal, Nov. 1990, pp. 195-203.*
International Search Report for PCT/IB2012/051650 mailed Sep. 11, 2012.
P. Mercer, "Measurement and Control of Barrier Layers", Tappi Journal, Nov. 1990, pp. 195-203.
Wilks Enterprise Inc., "Measuring Nylon , EVA or EVOH in a Multilayer Film with the InfraCal Filometer", Jan. 1, 2010, pp. 1-1.
Notice of Reasons for Rejection mailed Jan. 26, 2016, issued in Japanese Patent Application No. 2014-504417 and English translation.

* cited by examiner

*Primary Examiner* — Luke Ratcliffe
(74) *Attorney, Agent, or Firm* — Nixon & Vanderhye P.C.

(57) ABSTRACT

The invention relates to a device for detecting and/or determining the position of a barrier layer contained in the wall of a tubular packaging material. The device comprises an infrared source and an infrared receiver, said source and said receiver being placed so as to transmit (receive, respectively) infrared radiation through part of the wall of a tube containing a barrier layer to be analyzed. The invention also relates to a method of detecting and/or determining the position of a barrier layer contained in the wall of a tubular packaging material 15, the method comprising transmitting infrared radiation through a tube wall containing a barrier layer, receiving and analyzing said infrared radiation.

10 Claims, No Drawings

DEVICE AND METHOD FOR DETECTING AND/OR DETERMINING THE POSITION OF A BARRIER LAYER CONTAINED IN THE WALL OF A TUBULAR PACKAGING MATERIAL

This application is the U.S. national phase of International Application No. PCT/IB2012/051650 filed 4 Apr. 2012 which designated the U.S. and claims priority to EP 11162538.0 filed 15 Apr. 2011, the entire contents of each of which are hereby incorporated by reference.

FIELD OF THE INVENTION

The invention relates to the manufacturing of tubular packagings which contain a barrier layer, notably in the tube head. More specifically, the invention relates to the detection and/or the determining of the position of a barrier layer arranged in the wall of a tube.

STATE OF THE ART

Improving the barrier properties of packagings, and in particular of flexible tubes, has been the object of many developments, as much in terms of materials as in methods or technologies. The main difficulty that these works have made it possible to overcome has been the addition of barrier properties to the head of the tube which forms the top part of the packaging and which is linked to the flexible tubular body. The solutions described in the prior art can be classified in a number of categories:
  Tube heads obtained by assembling a barrier insert
  Tube heads obtained by overmolding a barrier insert
  Multilayer tube heads obtained by multi-material molding.

Numerous patents describe the methods and technologies that make it possible to implement the various solutions. The tube head can be fixed to the tubular body by welding or directly by overmolding.

However, when producing these barrier tubes in large quantities, a number of difficulties are encountered.

When the tube heads are manufactured by assembly, the heads are preassembled then packaged in boxes to then be transported to the tube production line. The boxes are emptied into hoppers, then the tube heads are routed to bowl feeders via conveyor belts and they are finally transferred to the welding station by guides. It is commonplace for an insert to be separated from the tube head before the assembly operation. This can cause production line stoppages when, for example, the insert becomes jammed in the guides. These frequent stoppages lower productivity and generate rejects associated with the starting up of the line. A second, much more critical problem is the manufacturing and the marketing of defective packagings. This problem occurs when a tube head without insert is welded onto the tubular body.

When the tube head is manufactured by overmolding an insert, similar difficulties are encountered.

When the tube head is manufactured by multilayer molding, it is impossible to control the correct distribution of the barrier layer in the tube head without destroying the packaging. It thus becomes very difficult for the producer to guarantee constant barrier properties for his packagings. Only long and tedious, a posteriori statistical checks can be used to inspect the quality of the samples produced. Since the inspection is not done in line, when a defective sample is detected, large quantities of packagings are rejected. This leads to significant waste as well as a loss of productivity.

There is therefore a significant need to be able to avoid producing defective packagings, to improve the productivity of the production lines, to reduce the quantity of waste and to guarantee a higher quality for the packagings produced.

EXPLANATION OF THE INVENTION

In order to resolve the abovementioned problems, the invention consists in using a device that makes it possible to detect and/or determine the distribution of a barrier layer contained in the wall of a tubular packaging. The device according to the invention comprises an infrared source and receiver (wavelength between 0.78 and 1000 microns) which are arranged in such a way as to emit—respectively receive—an infrared radiation which passes through a part of the wall of a tube containing a barrier layer to be analyzed.

The invention also relates to a method for detecting and/or determining the position of a barrier layer contained in the wall of a tubular packaging; the method comprising the emission of an infrared radiation through a tube wall containing a barrier layer, the reception and the analysis of said infrared radiation.

A barrier layer should be understood to be a layer of resin used to protect the packaged product from a gas or substance situated outside the packaging or to avoid the migration in the wall of the packaging or through the wall of the packaging of substances contained in the packaged product. It is common practice to use, for example, an oxygen barrier to avoid the oxidation of the packaged product or an aroma barrier to avoid the loss of aromas in the packaged product or even a light barrier to avoid the degradation of the product by light.

More specifically, the invention consists of a method for producing flexible tubes comprising at least two layers; said method comprising at least one source emitting a light with a wavelength preferably between 2 and 16 microns, said light passing through the tube wall to be analyzed, for example the head, during at least one step of the tube manufacturing method.

The manufacturing method makes it possible to avoid producing defective tubes and it more specifically makes it possible to guarantee a level of barrier properties in the head of the tube. The light passing through the wall to be analyzed is used either to detect the presence of a barrier layer, or to determine the distribution of the barrier layer in the tube head.

The method for manufacturing tubes contains a device that makes it possible to detect the barrier layer which is present in the tube head. This detection device consists of at least one light source, said light passing at least once through the tube head and having at least one wavelength of between 2 and 16 microns; and at least one receiver of said light measuring the light intensity of the transmitted light. It is observed that the light emitted by the source is strongly absorbed by the barrier layer of the tube head and fairly little by the other layers. A significant difference in light intensity is consequently obtained in the receiver between a tube head with and without barrier layer. This preferential absorption is particularly noted when the barrier layer is made of ethylene vinyl alcohol, polyethylene terephthalate or polyamide. For a light barrier, a black colored layer is often used and can be detected with the device.

It is observed that the intensity of the light received is weakly dependent on the base resin of which the tube head is composed and in particular if this resin is polyethylene or polypropylene. It is also observed that the base resin may contain pigments without that preventing the detection of the barrier layer. It is, however, noted that a black or very dark color significantly disrupts the detection, the absorption of this type of pigment in the infrared being close to or greater than the base resin. The black or very dark colored tube heads in the base resin are therefore to be avoided, and in general to be proscribed.

The detection device forms an integral part of the tube manufacturing method and makes it possible, depending on the case, to eject defective tube heads or tubes or accept packagings depending on the tolerances defined.

According to a first embodiment of the invention, the detection device is situated upstream of the assembly of the head and the cylindrical body. It is preferably situated downstream of the hopper feeding the shoulders or downstream of the bowl feeder. This configuration is preferred when the tubes are manufactured by welding the head onto the tubular body. The detection system is advantageously coupled to an ejection system situated downstream thereof, making it possible to eliminate the defective tube heads before assembly on the cylindrical body. Machine stoppages are avoided, and the manufacturing of defective tubes is eliminated.

According to a second embodiment of the invention, the detection device is situated after the assembly of the tube head on the tubular body. This configuration is preferred when the tube head is overmolded on the cylindrical body or when a risk of defect in assembly is identified. The detection system is advantageously coupled to an ejection system situated downstream and making it possible to eliminate the packagings that have defective tube heads.

There are many ways to produce the barrier layer detection device.

According to a first embodiment version of the detection device, the light emitter is situated on one side of the tube head and the light receiver facing the latter, on the other side of the tube head.

Another version consists in arranging the light emitter and the receiver on the same side of the tube head and using a light-reflecting mirror on the other side of the tube head.

The light source can be produced using a heated element (such as a bulb), a laser, a light-emitting diode, or other elements emitting infrared light. The emission device is chosen to emit at least one wavelength preferentially absorbed by the barrier layer of the tube head, said light being more weakly absorbed in the other layers of the tube head.

The receiver converts the intensity of the light received into an electrical signal that can be processed. Advantageously, the sensitivity of the detector is matched to the light-emitting source. The use of devices making it possible to select certain wavelengths such as filters, makes it possible to improve the detection of the barrier layer. Similarly, the use of devices that make it possible to influence the characteristics of the light emitted, such as polarizers or elements which modify the wavelength, can also make it possible to improve the detection.

In one version of the detection system, the light passing through the tube head originates from a spot source such as a diode or a focused laser and is received and analyzed at a point. This makes it possible to detect the presence or absence of the barrier layer at the measurement point. This method is particularly suited to detecting the barrier layer in the premanufactured shoulders comprising an insert.

In a more sophisticated version of the detection system, the analysis is done over the entire surface of the tube head in order to determine whether the barrier layer correctly covers the surface and in particular at the periphery of the tube head. An automatic image analysis system is advantageously coupled to this device.

The device and the method according to the invention make it possible to guarantee the barrier properties of 100% of the packagings produced.

The present invention makes it possible to reduce the production line stoppages and significantly limit the production waste.

The invention can advantageously be used in the context of manufacturing tubes comprising the following tube heads:

Tube head of polyethylene (PE) with a barrier layer of polyethylene terephthalate (PET).
Tube head of polyethylene (PE) with a barrier layer of ethylene vinyl alcohol (EVOH).
Tube head of polyethylene with a barrier layer of polyamide (PA).
Tube head of polyethylene with a barrier layer of black colored polyethylene.

The invention can also be used to detect the barrier layer in any other part of the tube such as, for example, in the tubular part or in the stopper. The tubular part is formed either by co-extrusion or by welding a multilayer sheet.

The invention has been described to improve the manufacturing of flexible tubes; however, there is a major benefit in also using the invention for the manufacturing of other types of packagings and in particular of packagings that have a multilayer molded part in which the barrier layer is captive and invisible.

The invention can be used to detect or determine the position of the barrier layer in packagings of "brick" type comprising a first part composed of a cardboard-based multilayer structure and a second molded part forming the neck. The invention makes it possible to detect or determine the position of the barrier layer in the neck of the packaging and also in the stopper if the latter has a multilayer structure.

The invention can be used advantageously for the manufacturing of flexible packagings manufactured from multilayer films and molded parts. Examples that can be mentioned include the flexible pockets comprising a multilayer neck. The invention is advantageous for detecting the barrier layer in the neck, it can also be used to detect the barrier layer in the multilayer film. A flexible packaging manufacturing variant consists in welding a neck and a bottom onto the flexible film to improve the stability of the packaging. The invention is used advantageously to detect the barrier layer in the bottom, in the neck and in the stopper.

One final example of use of the invention is the manufacturing of multilayer molded parts such as preforms or stoppers. The invention is advantageously used to improve the quality of the parts produced and reduce the waste by virtue of an in-line detection of the barrier layer in the molded objects.

The invention claimed is:
1. A device for at least one of detecting and determining the position of a barrier layer included in a wall of a tubular packaging, the device comprising:
an infrared source and a receiver, the source and the receiver being arranged to emit and respectively receive an infrared radiation which passes through a part of the wall of a tube of the tubular packaging including a barrier layer to be analyzed,
wherein the source and the receiver are adapted to emit and respectively receive an infrared radiation between 2 and 16 microns.

2. The device as claimed in claim 1, wherein the source and the receiver are arranged on either side of the wall of the tube to be analyzed.

3. The device as claimed in claim 1, wherein the source and the receiver are arranged on a same side of the tube to be analyzed, the device further comprising:
   a mirror arranged on the other side of the wall of the tube to be analyzed.

4. The device as claimed in claim 1, for at least one of detecting and determining the position of the barrier layer arranged in a head of the tube.

5. The device as claimed in claim 1, for at least one of detecting and determining the position of the barrier layer composed of ethylene vinyl alcohol, of polyethylene terephthalate, or of polyamide.

6. A system for manufacturing tubes comprising a unit for assembling tube heads on tubular bodies, the system comprising a device including:
   an infrared source and a receiver, the source and the receiver being arranged to emit and respectively receive an infrared radiation which passes through a tube head of a tubular body including a barrier layer to be analyzed,
   wherein the source and the receiver are adapted to emit and respectively receive an infrared radiation between 2 and 16 microns, and
   wherein the device is situated at least one of upstream and downstream of the assembly unit.

7. A method for at least one of detecting and determining a position of a barrier layer included in a wall of a tubular packaging, the method comprising the steps of:
   emitting an infrared radiation through the wall of a tube of the tubular packaging including the barrier layer; and
   receiving and analyzing of the infrared radiation,
   wherein the infrared radiation of the step of emitting has a wavelength between 2 and 16 microns.

8. The method as claimed in claim 7, wherein the infrared radiation is emitted prior to an assembly of a head on a body of the tubular packaging.

9. The system as claimed in claim 6, wherein the barrier layer is composed of ethylene vinyl alcohol, of polyethylene terephthalate, or of polyamide.

10. The method as claimed in claim 7, wherein the barrier layer is composed of ethylene vinyl alcohol, of polyethylene terephthalate, or of polyamide.

* * * * *